(12) United States Patent
Tagge et al.

(10) Patent No.: US 6,355,746 B1
(45) Date of Patent: Mar. 12, 2002

(54) COMPLEXES OF MID-TRANSITION METALS AND UNSATURATED NITROGENOUS LIGANDS AS SINGLE-SITE CATALYSTS

(75) Inventors: Christopher D. Tagge, San Carlos; Robert B. Wilson, Jr., Palo Alto, both of CA (US)

(73) Assignee: SRI International, Menlo Park, CA (US)

( * ) Notice: Subject to any disclaimer, the term of this patent is extended or adjusted under 35 U.S.C. 154(b) by 0 days.

(21) Appl. No.: 09/414,132

(22) Filed: Oct. 6, 1999

(51) Int. Cl.$^7$ .............................. C08F 4/22; C08F 4/78
(52) U.S. Cl. ...................... 526/133; 526/134; 526/161; 502/155
(58) Field of Search ................ 526/170, 171, 526/172, 348.6, 352, 351, 161, 133, 134; 502/155

(56) References Cited

U.S. PATENT DOCUMENTS

| | | |
|---|---|---|
| 3,691,095 A | 9/1972 | Kroll et al. |
| 5,459,117 A | 10/1995 | Ewen |
| 5,557,023 A | 9/1996 | Somogyvari et al. |
| 5,866,663 A | 2/1999 | Brookhart et al. |
| 6,162,884 A * | 12/2000 | Alt et al. ............... 526/161 |
| 6,214,761 B1 * | 4/2001 | Bennett ................ 502/117 |

FOREIGN PATENT DOCUMENTS

| | | |
|---|---|---|
| EP | 0416815 | 3/1991 |
| EP | 0874005 | 10/1998 |
| EP | 1008595 | 6/2000 |
| WO | WO 97/45434 | 12/1997 |
| WO | WO 98/03521 | 1/1998 |
| WO | WO 98/27124 | 6/1998 |
| WO | WO 98/30612 | 7/1998 |
| WO | WO 98/49208 | 11/1998 |
| WO | WO 98/12981 | 3/1999 |

OTHER PUBLICATIONS

Farahbakhsh et al. (1997), "Thio–Ligation to Vanadium: The *NSSN* and *S′ N′ O* Donor Sets (N = Pyridine, N= = Enamine; S = Thioether, S' = Thiolate),".

Gibson et al. (1998), "Chromium(III) Complexes Bearing N,N–Chelate Ligands as Ethene Polymerization Catalysts," *Chem. Commun.* 16:1651–1652.

Pal et al. (1994), "Dichlorochloro, Dichloro and Trichloro Complexes of Chromium(III) Containing Bidentate, Tridentate and Some Quadridentate Schiff Base Ligands," *J. Bangladesh Chem. Soc.* 7(2):126–137 (abstract only).

Vergopoulos et al. (1994), "Oxo and Non–Oxovanadium(IV) Complexes with Oxy–Carboxylate Ligands, and the Structure of VC12(Salen)," *Z. Naturforsch., B: Chem. Sci.* 49(8):1127–1136 (abstract only).

Westland et al. (1973), "Reactions of Halocarbonyls of Group VIb Elements. II. Complexes of Molybdenum and Tungsten Containing Group Va Donors or Phenyl Isocyanide," *Inorganic Chemistry* 12(10):2356–2361.

Horton (1994), "Metallocene Catalysts: Polymers by Design?," *Trends Polym. Sci.* 2(5):158–166.

Weidenbruch et al. (1993), "L Reaktionen von Silylenen und Disilenen mit 2,2'–Bipyridyl, Pyridin–2–aldiminen und α–Ketoiminen: Cycloadditionen versus C–H–Insertion," *Journal of Organometallic Chemistry* 454:35–43.

Feldman et al. (1997), "Electrophilic Metal Precursors and a β–Diimine Ligand for Nickel(II)– and Palladium(II)–Catalyzed Ethylene Polymerization," *Organometallics* 16(8): 1514–1516.

Hancock et al. (1976), "Bis(2,2'–Bipyridine) and Bis(1,10–phenanthroline) Complexes of Chromium(III) and Cobalt(III)," *Acta Chemica Scandinavica A* 30(2):79–97.

Johnson et al. (1995), "New Pd(II)–Based Catalysts for Polymerization of Ethylene and α–Olefins," *J. Am. Chem. Soc.* 117(23):6414–6415.

Johnson et al. (1996), "Copolymerization of Ethylene and Propylene with Functionalized Vinyl Monomers by Palladium(II) Catalysts," *J. Am. Chem. Soc.* 118(1):267–268.

Kim et al. (1998), "[(Ph)$_2$nacnac]MCI$_2$(THF)$_2$ (M = Ti, V, Cr): A New Class of Homogeneous Olefin Polymerization Catalysts Featuring β–Diiminate Ligands," *Organometallics* 17(21):4541–4543.

Zuech (1972), "Polymerizations with Homogeneous Chromium Catalysts," *Journal of Polymer Science; Polymer Chemistry Edition* 10:3665–3672.

\* cited by examiner

*Primary Examiner*—David W. Wu
*Assistant Examiner*—R. Harlan
(74) *Attorney, Agent, or Firm*—Dianne E. Reed; Reed & Associates

(57) ABSTRACT

Novel compounds are provided which are useful as catalysts, particularly in the polymerization of addition polymerizable monomers such as olefinic or vinyl monomers. The compounds are complexes of a mid-transition metal coordinated to at least two ligands, at least one of which is an unsaturated nitrogenous ligand. Depending on ligand substitution, stereospecific catalysts can be provided, including isospecific catalysts and syndiospecific catalysts. Catalyst systems containing the novel compounds in combination with a catalyst activator are provided as well, as are methods of using the novel compounds in the preparation of polyolefins.

35 Claims, No Drawings

COMPLEXES OF MID-TRANSITION METALS AND UNSATURATED NITROGENOUS LIGANDS AS SINGLE-SITE CATALYSTS

TECHNICAL FIELD

This invention relates generally to the field of catalysis, and more particularly relates to novel complexes of mid-transition metals and unsaturated nitrogenous ligands that are useful, inter alia, as polymerization catalysts. The invention additionally relates to methods for using the novel compounds as catalysts, particularly in the preparation of polymers such as polyolefins.

BACKGROUND

Many processes and catalysts are known for the preparation of homopolymeric or copolymeric olefins and other polymers. Ziegler-Natta catalyst compositions, developed in the 1950s, were found to be particularly useful in the preparation of polyolefins. These catalyst compositions comprise transition metal compounds such as titanium tetrachloride and an alkylaluminum (e.g., triethylaluminum) cocatalyst. The systems were found to be advantageous because of their high activity, and were largely consumed during polymerization.

Subsequent catalyst systems have been designed to provide more control over polymer structure and properties than could be achieved with Ziegler-Natta catalysts. These later catalysts have well-defined active sites and can be rationally designed to produce a specific polymer product, i.e., having predetermined structure and properties. Such catalysts include, for example, metal complexes known as "metallocenes." The term "metallocene" was initially coined in the early 1950s to refer to dicyclopentadienyliron, or "ferrocene," a structure in which an iron atom is contained between and associated with two parallel cyclopentadienyl groups. The term is now used to refer generally to organometallic complexes in which a metal atom (not necessarily iron) is coordinated to at least one cyclopentadienyl ring ligand. A. D. Horton, "Metallocene Catalysis: Polymers by Design," *Trends Polym. Sci.* 2(5):158–166 (1994), provides an overview of metallocene catalysts and their advantages, and focuses on now-conventional complexes of Group IV transition metal complexes and cyclopentadienyl ligands ($Cp_2MX_2$, wherein Cp represents a cyclopentadienyl ligand, M is Zr, Hf or Ti, and X is Cl or $CH_3$). Unfortunately, however, although metallocenes do provide significant advantages relative to the traditional Ziegler-Natta catalysts, the high cost and difficulties associated with heterogenization of metallocenes, as well as the oxophilic nature of the early transition metals, have limited the applicability of metallocenes as commercial polymerization catalysts.

Because polyolefins such as polyethylene and polypropylene are such important commercial polymers, there is an ongoing need for improved polymerization techniques and polymerization catalysts. Recently, researchers have developed new catalysts suitable for olefin polymerization that are complexes of late transition metals and substituted diimine ligands. Such catalysts are described, for example, in Bres et al., PCT Publication No. WO 98/49208, published Nov. 5, 1998. Other similar catalysts, comprised of diimine ligands and selected metals, are described in Bennett, PCT Publication No. WO 98/27174, published Jun. 25, 1998, and in Brookhart et al., PCT Publication No. WO 98/30612, published Jul. 16, 1998. While these catalysts have some advantages, they are lacking in several significant respects. Perhaps most importantly, the aforementioned catalysts are incapable of producing commodity polymers such as linear low density polyethylene ("LLDPE," having a density of about 0.918 to 0.935 $g/cm^3$) and isotactic polypropylene ("iPP").

The present invention is thus addressed to the aforementioned need in the art, and provides novel compounds useful as polymerization catalysts, e.g., in the polymerization of olefins. The catalysts provide for numerous advantages relative to the polymerization catalysts of the prior art, in that they:

(1) are simple and cost-effective to synthesize;
(2) allow for exceptional control over the structure and properties of the polymeric product;
(3) are highly active polymerization catalysts;
(4) can be used in stereospecific polymerization to provide stereoregular polymers, including isotactic and syndiotactic polymers;
(5) enable preparation of commodity polymers such as linear low density polyethylene and isotactic polypropylene;
(6) can be used as either supported or homogeneous polymerization catalysts;
(7) are quite versatile and can be used in conjunction with a variety of monomer types; and
(8) can be used to catalyze reactions other than polymerization reactions, e.g., hydrogenation.

The invention thus represents a significant advance in the field of catalysis, as prior to the development of the catalysts disclosed and claimed herein, only a few of the aforementioned advantages could be achieved with a single catalyst system.

SUMMARY OF THE INVENTION

Accordingly, it is a primary object of the invention to provide novel compounds useful as catalysts, particularly as polymerization catalysts.

It is another object of the invention to provide such compounds which are complexes of a mid-transition metal and at least one unsaturated nitrogenous ligand.

It is yet another object of the invention to provide such compounds containing two unsaturated nitrogenous ligands that are asymmetrically substituted, such that the compounds are useful as stereospecific catalysts.

It is still another object of the invention to provide such catalysts which are isospecific, thus enabling preparation of isotactic polymers.

It is another object of the invention to provide such catalysts which are syndiospecific, thus enabling preparation of syndiotactic polymers.

It is a further object of the invention to provide such compounds which are useful for preparing polyolefins or other polymers deriving from the polymerization of addition polymerizable monomers containing one or more degrees of unsaturation.

It is still a further object of the invention to provide catalyst systems containing a compound of the invention, a catalyst activator such as a metal alkyl, hydride, alkylhydride, alkylhalide or the like, and, optionally, additives such as inert diluents (e.g., a volatile hydrocarbon) and polymerization rate accelerators (e.g., Lewis bases, including amines and anilines).

It is yet a further object of the invention to provide a method for using the novel catalysts to prepare polyolefins or other polymers deriving from the polymerization of addition polymerizable monomers containing one or more degrees of unsaturation.

It is an additional object of the invention to provide a method for using the novel catalysts to prepare stereoregular polymers such as isotactic polypropylene.

It is still an additional object of the invention to provide a method for using the novel catalysts to prepare linear low density polyethylene.

Additional objects, advantages and novel features of the invention will be set forth in part in the description which follows, and in part will become apparent to those skilled in the art upon examination of the following, or may be learned by practice of the invention.

In one embodiment, the novel compounds have the structure $L^1[MQ^1Q^2]L^2$ in which M is a mid-transition metal, $Q^1$ and $Q^2$ are each a univalent radical, and $L^1$ and $L^2$ are ligands, wherein each of $L^1$ and $L^2$ contains a first coordinating atom that is a nitrogen atom contained within a C=N group, and a second coordinating atom that is either a second nitrogen atom, which may or may not be present in a second C=N group, or an oxygen, sulfur or phosphorus atom. Each C=N group may be a true imine functionality contained within an acyclic molecular segment, or may represent a linkage within a heterocycle such as a pyridine or pyrimidine ring. In this embodiment, the mid-transition metal M is selected from the group consisting of Nb, Ta, Mo, W, Mn and Re, and $L^1$ and $L^2$ may be covalently linked to each other, but typically represent separate and distinct ligands. Additionally, $L^1$ and $L^2$ may be the same or different. When a stereospecific catalyst is desired, $L^1$ and $L^2$ are substituted accordingly. That is, for an isospecific catalyst, the two ligands $L^1$ and $L^2$ are each asymmetrically substituted. For example, with a diimine ligand, one of the two imine nitrogens will be bound to a relatively small substituent, providing little or no steric bulk, while the other of the two imine nitrogens will be bound to a relatively large substituent, providing significant steric bulk, and the isospecific catalysts herein will contain two such ligands. For a syndiospecific catalyst, the two ligands $L^1$ and $L^2$ will differ substantially in size. Again, using diimine ligands for purposes of illustration, the imine nitrogen atoms of $L^1$ will typically be substituted with smaller substituents, while the imine nitrogen atoms of $L^2$ will typically be substituted with bulkier substituents. As will be appreciated by those skilled in the art, the stereoregularity of a polymer is an important aspect of molecular structure because it is a primary determinant of crystallinity. High stereoregular polymers typically have high crystallinity, while a nonstereoregular polymer is often amorphous (or of low crystallinity). Crystallinity, in turn, is a prime determinant of key physical properties such as stiffness, solvent resistance, and melting temperature. Thus, the fact that the present catalysts may be designed as stereospecific catalysts, useful in preparing polymers having predetermined stereoregularity, is a significant advantage of the invention.

The novel compounds may be positively charged, in which case they will be associated with a negatively charged counterion. Such complexes may be represented as $[L^1(MQ^1Q^2)L^2]^{+y} \cdot y/z[A^{-z}]$ wherein y and z are generally in the range of 1 to 4, more typically are 1 or 2, and A is any anion, e.g., halide, pseudohalide, or the like. It is to be understood that any compounds of the invention that are represented or drawn in neutral form, without any ionic charge indicated (e.g., as "$L^1[MQ^1Q^2]L^2$"), are also intended to encompass positively charged such compounds associated with an anion.

In another embodiment, the novel compounds are complexes having the structure $L^1[MQ^1Q^2]L^AL^B$ as shown in formula (I)

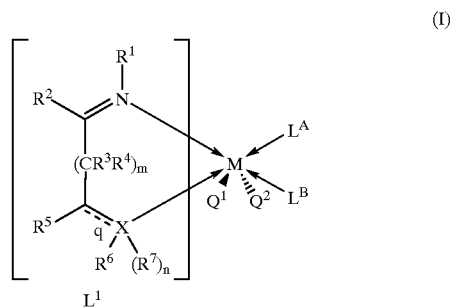

(I)

wherein:
M is a mid-transition metal, i.e., a metal selected from Groups VA, VIA and VIIA of the periodic table of the elements;
$Q^1$ and $Q^2$ are independently selected from the group consisting of hydrido, halide, alkoxy, amido, unsubstituted $C_1-C_{30}$ hydrocarbyl, $C_1-C_{30}$ hydrocarbyl substituted with one or more substituents such as electron-withdrawing groups, and $C_1-C_{30}$ hydrocarbyl-substituted Group IVB elements, or $Q^1$ and $Q^2$ may together form an alkylidene olefin, acetylene, or a five- or six-membered cyclic hydrocarbyl group;
m and n are independently zero or 1;
q is an optional double bond;
X is N, O, S or P, with the provisos that (a) when X is N or P, then either n is 1 or q is present as a double bond, but not both, and (b) when X is O or S, then n is zero and q is absent;
$R^1$, $R^6$, and $R^7$ are independently hydrido, hydrocarbyl or substituted hydrocarbyl, and $R^2$ and $R^5$ are independently hydrido, halo, hydrocarbyl or substituted hydrocarbyl, or $R^1$ and $R^2$ and/or $R^5$ and $R^6$ may be taken together to form a linkage —Q—, resulting in a five- or six-membered ring, wherein Q is —[(CR)$_a$(Z)$_b$]— in which a is 2, 3 or 4, Z is N, O or S, b is zero or 1, the sum of a and b is 3 or 4, and R is selected from the group consisting of hydrido, halo, hydrocarbyl, hydrocarbyloxy, trialkylsilyl, $NR^8_2$, $OR^9$, and $NO_2$, wherein $R^8$ and $R^9$ are each independently hydrocarbyl, or wherein R moieties on adjacent carbon atoms may be linked to form an additional five- or six-membered ring, or $R^2$ and $R^5$ may together form a linkage —Q— as just defined;
$R^3$ and $R^4$ are independently selected from the group consisting of hydrido and hydrocarbyl, or at least one of $R^3$ and $R^4$ may be bound through a lower alkylene linkage to an atom contained within $L^A$ or $L^B$;

$L^A$ and $L^B$ are ligands which may be the same or different and are independently selected from the group consisting of nitrogen-containing, sulfur-containing and oxygen-containing heterocycles, tertiary amines and phosphines, or $L^A$ and $L^B$ may together form a single bidentate such as ligand $L^2$ where $L^2$ is as defined previously, and wherein $L^2$ may or may not be the same as $L^1$, with the proviso that when (a) $L^A$ and $L^B$ form $L^2$, (b) $L^2$ is identical to $L^1$, and (c) M is V or Cr, then either (d) $R^1$ and $R^2$ or $R^5$ and $R^6$ are taken together to form a linkage Q as defined above, or (e) X is other than N, or both (d) and (e).

When $L^A$ and $L^B$ together form a single bidentate ligand $L^2$, preferred complexes have the formula (II)

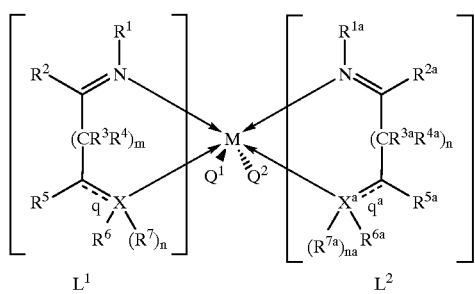

wherein:

M is a mid-transition metal, i.e., metal selected from Groups VA, VIA and VIIA of the periodic table;

$Q^1$ and $Q^2$ are as defined for structural formula (I); and $q^a$, ma, na, $R^{1a}$, $R^{2a}$, $R^{3a}$, $R^{4a}$, $R^{5a}$, $R^{6a}$ and $R^{7a}$ are defined as for q, m, n, $R^1$, $R^2$, $R^3$, $R^4$, $R^5$, $R^6$ and $R^7$, respectively.

In a related embodiment, novel compounds are provided having the structure of formula (III)

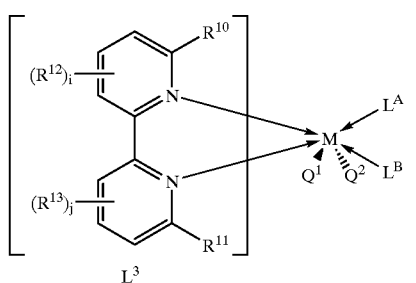

wherein i and j are independently zero, 1, 2 or 3, $R^{10}$, $R^{11}$, $R^{12}$ and $R^{13}$ are independent hydrocarbyl or substituted hydrocarbyl, and M, $Q^1$, $Q^2$, $L^A$ and $L^B$ are as defined previously, or $L^A$ and $L^B$ together represent an additional $L^3$ moiety.

In a further embodiment, complexes having the structure of formula (IV) are provided

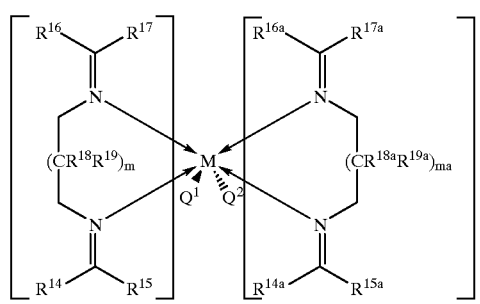

wherein:

M is a mid-transition metal selected from Groups VA, VIA and VIIA of the periodic table of the elements;

$Q^1$ and $Q^2$ are as defined above for structural formulae (I) and (II);

$R^{14}$ is hydrocarbyl or substituted hydrocarbyl, and $R^{15}$ is hydrido, hydrocarbyl or substituted hydrocarbyl, or $R^{14}$ and $R^{15}$ taken together form a ring;

$R^{14a}$ is hydrocarbyl or substituted hydrocarbyl, and $R^{15a}$ is hydrido, hydrocarbyl or substituted hydrocarbyl, or $R^{14a}$ and $R^{15a}$ taken together form a ring;

$R^{16}$ is hydrocarbyl or substituted hydrocarbyl, and $R^{17}$ is hydrido, hydrocarbyl or substituted hydrocarbyl, or $R^{16}$ and $R^{17}$ taken together form a ring;

$R^{16a}$ is hydrocarbyl or substituted hydrocarbyl, and $R^{17a}$ is hydrido, hydrocarbyl or substituted hydrocarbyl, or $R^{16a}$ and $R^{17a}$ taken together form a ring;

$R^{18}$, $R^{18a}$, $R^{19}$ and $R^{19a}$ are independently selected from the group consisting of hydrido and hydrocarbyl, or one of $R^{18}$ and $R^{18a}$ may be bound to one of $R^{19}$ and $R^{19a}$ through a lower alkylene linkage; and m and ma are independently zero or 1.

The compounds of the invention, as alluded to above, may be positively charged and thus associated with a negatively charged counterion. That is, a metal complex of formulae (I), (II), (III) or (IV) may carry a positive charge +y, where y is an integer in the range of 1 through 4, more typically 1 or 2, and is associated with y/z anions each bearing a negative charge −z.

In an additional embodiment of the invention, a catalyst system is provided comprised of (1) a compound of the invention, as a catalyst, and (2) a catalyst activator such as a metal alkyl, hydride, alkylhydride, alkylhalide or the like, effective to convert the catalyst to a catalytically active ionic species. An exemplary catalyst is activator is methyl aluminoxane ("MAO"). Generally, the catalyst system will also contain an inert diluent, e.g., a hydrocarbon solvent, and optional additives such as polymerization rate accelerators. In catalyzing reactions, e.g., polymerization reactions, hydrogenation reactions, and the like, the compounds of the invention are used in such a catalyst system. Typically, polymerization involves conventional processes wherein selected monomers are contacted with a compound of the invention under reaction conditions effective to provide the desired polymer composition or other product.

In addition to their utility as polymerization catalysts, the novel compounds are also useful in catalyzing other types of reactions, e.g., hydrogenation, dehydrocoupling, cyclization, substitution, carbomagnesation and hydrosilylation.

DETAILED DESCRIPTION OF THE INVENTION

Definitions and Nomenclature

Before the present compounds, compositions and methods are disclosed and described, it is to be understood that unless otherwise indicated this invention is not limited to specific molecular structures, ligands, or the like, as such may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a substituent" includes one or more substituents, reference to "a ligand" includes one or more ligands, and the like.

The term "alkyl" as used herein refers to a branched or unbranched saturated hydrocarbon group of 1 to approximately 24 carbon atoms, typically 1 to approximately 12 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl and the like. The term "lower alkyl" intends an alkyl group of 1 to 6 carbon atoms, preferably 1 to 4 carbon atoms.

The term "alkylene" as used herein refers to a difunctional saturated branched or unbranched hydrocarbon chain containing from 1 to approximately 24 carbon atoms, typically 1 to approximately 12 carbon atoms, and includes, for example, methylene (—$CH_2$—), ethylene (—$CH_2$—$CH_2$—), propylene (—$CH_2$—$CH_2$—$CH_2$—), 2-methylpropylene (—$CH_2$—$CH(CH_3)$—$CH_2$—), hexylene (—$(CH_2)_6$—), and the like. "Lower alkylene" refers to an alkylene group of 1 to 6, more preferably 1 to 4, carbon atoms.

The term "alkenyl" as used herein refers to a branched or unbranched hydrocarbon group of 2 to approximately 24 carbon atoms, typically 2 to approximately 12 carbon atoms, containing at least one carbon-carbon double bond, such as ethenyl, n-propenyl, isopropenyl, n-butenyl, isobutenyl, t-butenyl, octenyl, decenyl, tetradecenyl, hexadecenyl, eicosenyl, tetracosenyl and the like. Preferred alkenyl groups herein contain 2 to 12 carbon atoms and 2 to 3 carbon-carbon double bonds. The term "lower alkenyl" intends an alkenyl group of 2 to 6 carbon atoms, preferably 2 to 4 carbon atoms, containing one —C=C— bond. The term "cycloalkenyl" intends a cyclic alkenyl group of 3 to 8, preferably 5 or 6, carbon atoms.

The term "alkenylene" refers to a difunctional branched or unbranched hydrocarbon chain containing from 2 to approximately 24 carbon atoms, typically 2 to approximately 12 carbon atoms, and at least one carbon-carbon double bond. "Lower alkenylene" refers to an alkenylene group of 2 to 6, more preferably 2 to 5, carbon atoms, containing one —C=C— bond.

The term "alkynyl" as used herein refers to a branched or unbranched hydrocarbon group of 2 to approximately 24 carbon atoms, as above containing at least one —C≡C— bond, such as ethynyl, n-propynyl, isopropynyl, n-butynyl, isobutynyl, t-butynyl, octynyl, decynyl and the like. Preferred alkynyl groups herein contain 2 to 12 carbon atoms. The term "lower alkynyl" intends an alkynyl group of 2 to 6, preferably 2 to 4, carbon atoms, and one —C≡C— bond.

The term "alkynylene" refers to a difunctional branched or unbranched hydrocarbon chain containing from 2 to approximately 24 carbon atoms as before and at least one carbon-carbon triple bond. "Lower alkynylene" refers to an alkynylene group of 2 to 6, more preferably 2 to 5, carbon atoms, containing one —C≡C— bond.

The term "alkoxy" as used herein intends an alkyl group bound through a single, terminal ether linkage; that is, an "alkoxy" group may be defined as —OR where R is alkyl as defined above. A "lower alkoxy" group intends an alkoxy group containing one to six, more preferably one to four, carbon atoms.

The term "aryl" as used herein refers to an aromatic species containing 1 to 5 aromatic rings, either fused or linked, and either unsubstituted or substituted with 1 or more substituents typically selected from the group consisting of —$(CH_2)_x$—$NH_2$, —$(CH_2)_x$—COOH, —$NO_2$, halogen, alkyl, alkenyl, alkynyl, alkoxy, alkenyloxy, alkynyloxy, alkylthio, aryl, aralkyl, and the like, where x is an integer in the range of 0 to 6 inclusive as outlined above. Preferred aryl substituents contain 1 to 3 fused aromatic rings, and particularly preferred aryl substituents contain 1 aromatic ring or 2 fused aromatic rings. The terms "aralkyl" and "alkaryl" refer to moieties containing both alkyl and aryl species, typically containing less than about 24 carbon atoms, and more typically less than about 12 carbon atoms in the alkyl segment of the moiety, and typically containing 1 to 5 aromatic rings. The term "aralkyl" refers to aryl-substituted alkyl groups, while the term "alkaryl" refers to alkyl-substituted aryl groups. The terms "aralkylene" and "alkarylene" are used in a similar manner to refer to aryl-substituted alkylene and alkyl-substituted arylene moieties.

The term "arylene" refers to a difunctional aromatic moiety; "monocyclic arylene" refers to a cyclopentylene or phenylene group. These groups may be substituted with up to four ring substituents as outlined above.

The term "heterocyclic" refers to a five- or six-membered monocyclic structure or to an eight- to eleven-membered bicyclic structure which is either saturated or unsaturated. Each heterocycle consists of carbon atoms and from one to four heteroatoms selected from the group consisting of nitrogen, oxygen and sulfur. As used herein, the terms "nitrogen heteroatoms" and "sulfur heteroatoms" include any oxidized form of nitrogen and sulfur, and the quaternized form of any basic nitrogen. Examples of heterocyclic groups include piperidinyl, pyrazinyl, morpholinyl and pyrrolidinyl.

"Halo" or "halogen" refers to fluoro, chloro, bromo or iodo, and usually relates to halo substitution for a hydrogen atom in an organic compound. Of the halos, chloro and fluoro are generally preferred.

"Hydrocarbyl" refers to univalent unsubstituted and substituted hydrocarbyl radicals containing 1 to about 30 carbon atoms, typically 1 to about 24 carbon atoms, preferably 1 to about 12 carbon atoms, including branched or unbranched, saturated or unsaturated species, such as alkyl groups, alkenyl groups, aryl groups, heteroaryl groups, and the like. The term "lower hydrocarbyl" intends a hydrocarbyl group of one to six carbon atoms, preferably one to four carbon atoms. The term "hydrocarbylene" intends a divalent unsubstituted or unsubstituted hydrocarbyl moiety, including branched or unbranched, saturated or unsaturated species, or the like. The term "lower hydrocarbylene" intends a hydrocarbylene group of 1 to 6 carbon atoms, preferably 1 to 4 four carbon atoms. The term "hydrocarbyloxy" or "hydrocarbylthio" refer to a hydrocarbyl group bound through a terminal ether or thio linkage.

By "substituted" as in "substituted hydrocarbyl" or "substituted hydrocarbylene" is meant that the hydrocarbyl or hydrocarbylene group contains one or more substituent groups which are inert under the process conditions to which the compound containing these groups is subjected. The substituent group may replace a hydrogen atom or may be found as a linkage within the carbon chain. "Monosubstituted" refers to a hydrocarbyl or hydrocarbylene group having one substituent group and "disubstituted" refers to a hydrocarbyl or hydrocarbylene group containing two substituted groups. The substituent groups also do not substantially interfere with the process. Included in the meaning of "substituted" are heteroaromatic rings. Examples of substituents include, but are not limited to, amino (including primary amino and alkyl-substituted, typically lower alkyl-substituted, secondary and tertiary amino), alkyl (typically lower alkyl), alkoxy (typically lower alkoxy), alkenyl (typically lower alkenyl), aryl (e.g., phenyl), halo, haloalkyl, imino, nitro, and the like; "substituted" also refers to the replacement of a carbon atom in a hydrocarbyl or hydrocarbylene group with a non-hydrocarbyl linkage such as —O—, —S—, —NH—, —N(alkyl)—, etc.

The term "unsaturated nitrogenous compound" refers to a compound having a C=N moiety. Unsaturated nitrogenous compounds herein include both a true imine wherein the C=N moiety is present in an acyclic molecular segment, as well as nitrogenous heterocycles in which the carbon-nitrogen bond is present in an aromatic ring, e.g., as in pyridine, pyrimidine, pyrazine, and the like.

Unless otherwise indicated, the term "mid-transition metal" refers to any metal selected from Groups VA, VIA and VIIA of the periodic table (using the IUPAC system for naming chemical elements). Exemplary mid-transition metals include, but are not limited to, Mb, Ta, Mo, W, Mn, Re, V and Cr.

"Optional" or "optionally" means that the subsequently described event or circumstance may or may not occur, and that the description includes instances where said event or circumstance occurs and instances where it does not. For example, the phrase "optionally substituted hydrocarbyl" means that a hydrocarbyl moiety may or may not be substituted and that the description includes both unsubstituted hydrocarbyl and hydrocarbyl where there is substitution.

A "heterogeneous" catalyst as used herein refers to a catalyst which is supported on a carrier, typically although not necessarily a substrate comprised of an inorganic, solid, particulate porous material such as silicon and/or aluminum oxide.

A "homogeneous" catalyst as used herein refers to a catalyst which is not supported but is simply admixed with the initial monomeric components in a suitable solvent.

The term "stereoregularity" is used in the conventional sense to refer to the relative positioning of substituent groups of monomer units in a polymer chain. The term "stereostructure" refers to the stereoregularity of any particular polymer. Possible polymeric stereostructures include the following: atactic polymers, in which the arrangement of substituents is random; isotactic polymers, in which all substituents are identically oriented; syndiotactic polymers, in which the orientation of substituents alternates; stereoblock polymers, containing blocks of monomers all oriented the same way, and blocks of monomers all oriented the opposite way; isoblock polymers, containing blocks of isotactic monomer units separated by a single oppositely oriented monomer unit; hemiisotactic polymers, having every other monomer unit oriented in the same way (isotactic), separated by a monomer that is randomly oriented; and hemisyndiotactic polymers having every other monomer unit oriented in the opposite way (syndiotactic), separated by a randomly oriented monomer unit.

By "stereospecific" is meant a catalyst that will provide a polymer of predetermined, desired stereoregularity. The preferred catalysts herein are "stereospecific." By "isospecific" is meant a catalyst that will provide an isotactic polymer. By "syndiospecific" is meant a catalyst that will provide a syndiospecific polymer. The most preferred catalysts herein are "isospecific" and "syndiospecific."

As used herein all reference to the Periodic Table of the Elements and groups thereof is to the version of the table published by the Handbook of Chemistry and Physics, CRC Press, 1995, which uses the IUPAC system for naming groups.

The Novel Compounds

In a first embodiment, then, the compounds of the invention are organometallic complexes represented by the formula $L^1[MQ^1Q^2]L^2$ in which M is a mid-transition metal, $Q^1$ and $Q^2$ are each a univalent radical, and $L^1$ and $L^2$ are ligands, wherein each of $L^1$ and $L^2$ is an unsaturated nitrogenous ligand. $L^1$ and $L^2$ may identical, or they may be different; in addition, they may represent separate and distinct ligands, or they may be covalently linked to each other.

In this embodiment, the mid-transition metal "M" is selected from the group consisting of Mb, Ta, Mo, W, Mn and Re.

$Q^1$ and $Q^2$ are each a univalent radical, and are preferably independently selected from the group consisting of hydrido, halide, alkoxy, amido, and substituted or unsubstituted $C_1$–$C_{30}$ hydrocarbyl; if substituted, the substituents are typically although not necessarily electron-withdrawing groups such as a halogen atom, an alkoxy group, or the like, or the substituents may be Group IVB elements. Alternatively, $Q^1$ and $Q^2$ may together form an alkylidene olefin (i.e., =$CR_2$ wherein R is hydrogen or hydrocarbyl, typically lower alkyl), acetylene, or a five- or six-membered cyclic hydrocarbyl group. Preferred $Q^1$ and $Q^2$ moieties are hydrido, amido, $C_1$–$C_{12}$ alkyl, and $C_1$–$C_{12}$ alkyl substituted with one or more halogen and/or alkoxy groups, typically one to six such groups, and $C_1$–$C_{12}$ alkyl substituted with a Group IVB element. Particularly preferred $Q^1$ and $Q^2$ moieties are hydrido, amido, lower alkyl and lower alkoxy.

$L^1$ and $L^2$ are unsaturated nitrogenous ligands. More particularly, each of $L^1$ and $L^2$ contains a first coordinating atom that is a nitrogen atom contained within a C=N group, and a second coordinating atom that is either a second nitrogen atom, which may or may not be present in a second C=N group, or an oxygen, sulfur or phosphorus atom. Each C=N group may be a true imine functionality contained within an acyclic molecular segment, or may represent a linkage within a heterocycle such as a pyridine or pyrimidine ring.

In another embodiment, the novel compounds are complexes having the structure $L^1[MQ^1Q^2]L^AL^B$ as shown in formula (I)

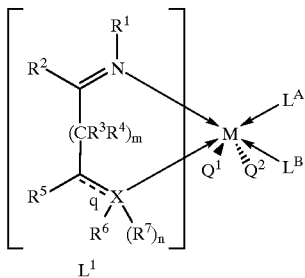

wherein the various substituents are defined as follows.

M is a mid-transition metal, i.e., a metal selected from Groups VA, VIA and VIIA of the periodic table of the elements. Preferred mid-transition metals in this embodiment are Mb, Ta, Mo, W, Mn, Re, V and Cr.

$Q^1$ and $Q^2$ are each univalent radicals, as defined earlier herein.

The subscripts m and n are independently zero or 1, preferably are both zero, and letter "q" represents an optional double bond.

X is N, O, S or P, with the provisos that (a) when X is N or P, then either n is 1 or q is present as a double bond, but not both, and (b) when X is O or S, then n is zero and q is absent.

$R^1$, $R^6$ and $R^7$ are independently hydrido, hydrocarbyl or substituted hydrocarbyl, as defined above, and $R^2$ and $R^5$ are independently hydrido, halo, hydrocarbyl or substituted hydrocarbyl, also as defined above, or $R^1$ and $R^2$ and/or $R^5$ and $R^6$ may be taken together to form a linkage —Q—, resulting in a five- or six-membered cyclic group. Similarly, $R^2$ and $R^5$ may together form a linkage —Q—. As explained above, Q is —[(CR)$_a$(Z)$_b$]— in which a is 2, 3 or 4, Z is N, O or S, b is zero or 1, the sum of a and b is 3 or 4, and R is selected from the group consisting of hydrido, halo, hydrocarbyl, hydrocarbyloxy, trialkylsilyl, $NR^8{}_2$, $OR^9$, and $NO_2$, wherein $R^8$ or $R^9$ are each independently hydrocarbyl, or wherein R moieties on adjacent carbon atoms may be linked to form an additional five- or six-membered ring.

Examples of $R^1$, $R^6$ and $R^7$ thus include, but are not limited to, hydrido, methyl, ethyl, n-propyl, isopropyl, methoxy, ethoxy, isopropoxy, phenyl, benzyl, phenoxy, pyridyl, diisopropylphenyl, methoxyphenyl, trimethylsilyl, triethylsilyl, and the like; $R^2$ and $R^5$ substituents can include any of the foregoing as well as halogen substituents, i.e., chloro, fluoro, bromo and iodo, with chloro and fluoro preferred. When $R^1$ and $R^2$ and/or $R^5$ and $R^6$ are linked, the cyclic structures so formed may be alicyclic or aromatic, including, for example, furanyl, pyrrolyl, thiophenyl, imidazolyl, pyrazolyl, oxathiolyl, pyridinyl, methylpyridinyl, ethylpyridinyl, pyridazinyl, pyrimidinyl, pyrazinyl, piperidinyl, piperazinyl, morpholinyl, tetrahydrothiophenyl, tetrahydrofuranyl, tetrahydropyranyl, 1,4-dioxanyl, etc. When $R^2$ and $R^5$ are linked, the resulting structures are alicyclic and may or may not contain heteroatoms; such moieties include, for example, cyclopentane, cyclohexane, tetrahydrofuran, tetrahydropyran, tetrahydrothiophene, 1,4-dioxane, 1,2-dithiole, 1,3-dithiole, piperazine, morpholine, and the like.

$R^3$ and $R^4$ are independently selected from the group consisting of hydrido and hydrocarbyl, preferably hydrido or lower alkyl, or at least one of $R^3$ and $R^4$ may be bound through a lower alkylene linkage, preferably a methylene linkage, to an atom contained within $L^A$ or $L^B$.

$L^A$ and $L^B$ are ligands which may be the same or different and are generally selected from: nitrogen-containing heterocycles such as pyridine, pyridazine, pyrimidine, pyrazine, 1,3,5-triazine, 1,2,4-triazine, 1,2,3-triazine, pyrrole, 2H-pyrrole, 3H-pyrrole, pyrazole, 2H-imidazole, 1,2,3-triazole, 1,2,4-triazole, indole, 3H-indole, 1H-isoindole, cyclopenta(b)pyridine, indazole, quinoline, isoquinoline, cinnoline, quinazoline, naphthyridine, piperidine, piperazine, pyrrolidine, pyrazolidine, quinuclidine and imidazolidine; sulfur-containing heterocycles such as thiophene, 1,2-dithiole, 1,3-dithiole, thiepin, benzo(b)thiophene and benzo(c)thiophene; oxygen-containing heterocycles such as 2H-pyran, 4H-pyran, 2-pyrone, 4-pyrone, 1,2-dioxin, 1,3-dioxin, oxepin, furan, 2H-1-benzopyran, coumarin, chroman-4-one, isochromen-1-one, isochromen-3-one, xanthene, tetrahydrofuran and 1,4-dioxan; mixed heterocycles such as isoxazole, oxazole, thiazole, isothiazole, 1,2,3-oxadiazole, 1,2,4-oxadiazole, 1,3,4-oxadiazole, 1,2,3,4-oxatriazole, 1,2,3,5-oxatriazole, 3H-1,2,3-dioxazole, 3H-1,2-oxathiole, 1,3-oxathiole, 4H-1,2-oxazine, 2H-1,3-oxazine, 1,4-oxazine, 1,2,5-oxathiazine, o-isooxazine, pyrano[3,4-b]pyrrole, indoxazine, benzoxazole, anthranil and morpholine; tertiary amines, particularly trialkylamines, and preferably tri(lower alkyl) amines such as triethylamine, methyldiethylamine, trimethylamine, methyldiisopropylamine, and the like; phosphines, particularly trialkylphosphines, and preferably tri(lower alkyl)phosphines such as triethylphosphine, methyldiethylphosphine, trimethylphosphine, methyldiisopropylphosphine, and the like. Alternatively, $L^A$ and $L^B$ may together form a single bidentate ligand such as $L^2$ or $L^3$ where $L^2$ and $L^3$ are as defined previously, and wherein the ligand may or may not be the same as $L^1$, with the proviso that when (a) $L^A$ and $L^B$ form $L^2$, (b) $L^2$ is identical to $L^1$, and (c) M is V or Cr, then either (d) $R^1$ and $R^2$ or $R^5$ and $R^6$ are taken together to form a linkage —Q— as defined above, or (e) X is other than N, or both (d) and (e).

The complex may be electronically neutral, or it may be charged, depending on the selected metal and its oxidation state. That is, compounds of the invention may also be represented as $[L^1(MQ^1Q^2)L^2]^{+y} \cdot y/z[A^{-z}]$ wherein y and z are generally in the range of 1 to 4, more typically are 1 or 2, and A is any anion. A may be, for example, a halide or pseudohalide ion, or a fluorohydrocarbylborate such as tetra(pentafluorophenyl)borate, sodium tetrakis[(bis-3,5-trifluoromethyl)phenyl]borate, H+(OCH$_2$CH$_3$)$_2$[(bis-3,5-trifluoromethyl)phenyl]borate, trityltetra(pentafluorophenyl)borate and tris(pentafluorophenyl)boron.

When $L^A$ and $L^B$ together form a single bidentate ligand $L^2$, preferred such structures have the formula (II)

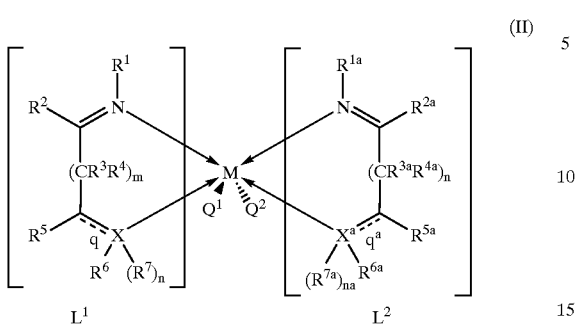

(II)

wherein

M, $Q^1$ and $Q^2$ are as defined above with respect to the structure of formula (I), and $q^a$, ma, na, $R^{1a}$, $R^{2a}$, $R^{3a}$, $R^{4a}$, $R^{5a}$, $R^{6a}$ and $R^{7a}$ are defined as q, m, n, $R^1$, $R^2$, $R^3$, $R^4$, $R^5$, $R^6$ and $R^7$, respectively. The ligands $L^1$ and $L^2$ may be the same or different, and they are optionally linked, either directly or indirectly, through one or more covalent bonds. For example, one of $R^3$ and $R^{3a}$ may be bound to one of $R^4$ and $R^{4a}$ through a lower alkylene linkage, preferably a methylene linkage.

Again, compounds of formula (II) may be electronically neutral or they may be positively charged and associated with a negatively charged anion, as explained above.

An example a preferred type of catalyst encompassed by structural formula (II) is shown in formula (V), as follows:

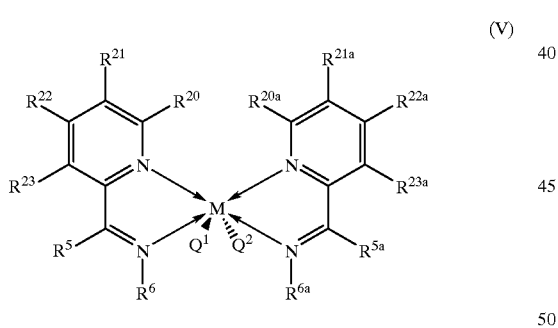

(V)

wherein M, $Q^1$, $Q^2$, $R^5$, $R^{5a}$, $R^6$ and $R^{6a}$ are as defined above with respect to the structures of formulae (I), (II), (III) and (IV), and $R^{20}$, $R^{20a}$, $R^{21}$, $R^{21a}$, $R^{22}$, $R^{22a}$, $R^{23}$ and $R^{23a}$ are preferably hydrido or hydrocarbyl of 1 to 10 carbon atoms, or any two adjacent $R^{20}$, $R^{20a}$, $R^{21}$, $R^{21a}$, $R^{22}$, $R^{22a}$, $R^{23}$ and $R^{23a}$ groups may be linked to form a further ring or rings, for example a benzene ring. Specific examples of $R^{20}$, $R^{20a}$, $R^{21}$, $R^{21a}$, $R^{22}$, $R^{22a}$, $R^{23}$ and $R^{23a}$ include, but are not limited to, methyl, ethyl, n-propyl, n-butyl, n-hexyl and n-octyl, although most preferably, $R^{20}$, $R^{20a}$, $R^{21}$, $R^{21a}$, $R^{22}$, $R^{22a}$, $R^{23}$ and $R^{23a}$ are all hydrogen.

An example of a particularly preferred catalyst encompassed by structural formula (V) is shown in formula (VI), as follows:

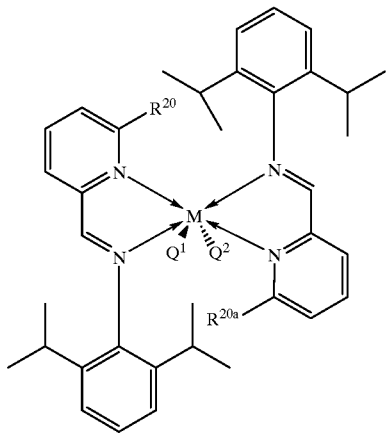

(VI)

wherein M, $Q^1$, $Q^2$, $R^{20}$ and $R^{20a}$ are as defined above with respect to the structure of formula (V); optimally, in structure (VI), $R^{20}$ and $R^{20a}$ are both hydrido. This catalyst is representative of those catalysts of the invention that are isospecific, insofar as each ligand is asymmetrically substituted, having a bulky molecular segment appended to one of the nitrogen atoms, and a smaller molecular segment appended to the second of the nitrogen atoms.

Another example of stereospecific catalyst encompassed by structural formula (II) is shown in formula (VII), as follows.

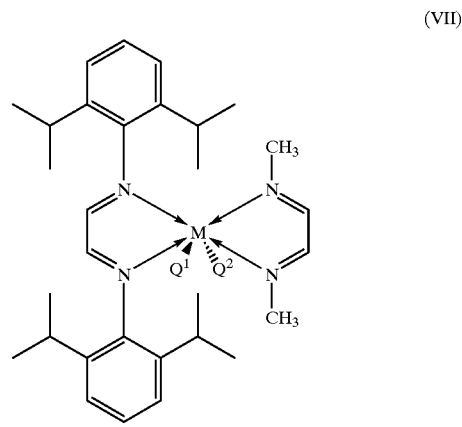

(VII)

This catalyst is representative of those catalysts of the invention that are generally syndiospecific, insofar as one ligand is substituted with bulky (2,4-diisopropylphenyl) substituents, while the other ligand is substituted with far smaller (methyl) substituents.

Asymmetric substitution and its correlation to stereospecificity, and particularly isospecificity and syndiospecificity, may be illustrated as follows:

(VIII)

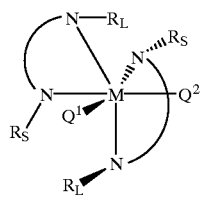

In structure (VIII), $R_S$ represents a relatively small substituent, while $R_L$ represents a relatively large, sterically bulky substituent. Such a catalyst is "isospecific" and may be used to prepare isotactic polyolefins, e.g., isotactic polypropylene, which has far more commercial value than atactic polypropylene.

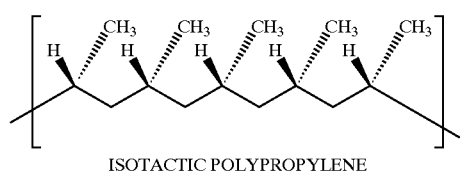

ISOTACTIC POLYPROPYLENE

In contrast to the atactic polymer, isotactic polypropylene is a high melting, strong, crystalline polymer, useful in a variety of industrial contexts, e.g., as a plastic, as a fiber, and the like. The stereospecific catalysts of the invention can also be used to provide other isotactic polymers, including isotactic poly(1-butene) and poly(4-methyl-1-pentene).

(IX)

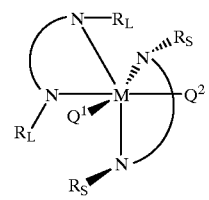

is generally syndiospecific, insofar as one ligand contains two sterically bulky "$R_L$" substituents, and the other ligand contains two relatively small "$R_S$" substituents. The relative steric bulk of RL and RS provides for a syndiospecific catalyst, which can be used in stereospecific polymerization to prepare syndiotactic polymers such as syndiotactic polypropylene.

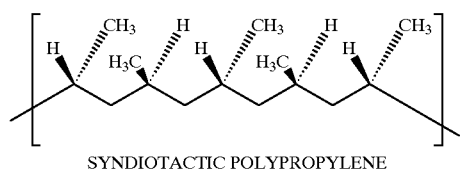

SYNDIOTACTIC POLYPROPYLENE

It should be emphasized that any of the foregoing metal complexes may be either electronically neutral or positively charged, wherein, in the latter case, the complex will be associated with a negatively charged counterion.

The catalysts of the invention are also useful to prepare linear low density polyethylene, a preferred type of polyethylene for many commercial uses, wherein the polymer contains up to about 10% of a comonomer such as 1-butene, 1-hexene, 1-octene or 4-methyl-1-pentene.

Specific catalysts encompassed by formula (I) include, but are not limited to, the following:

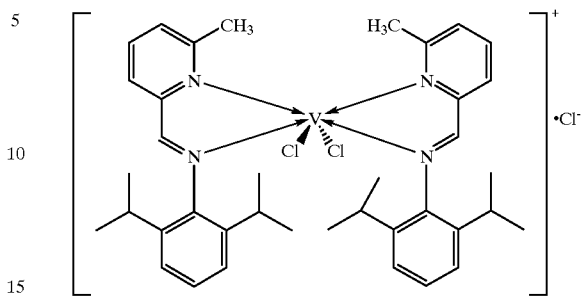

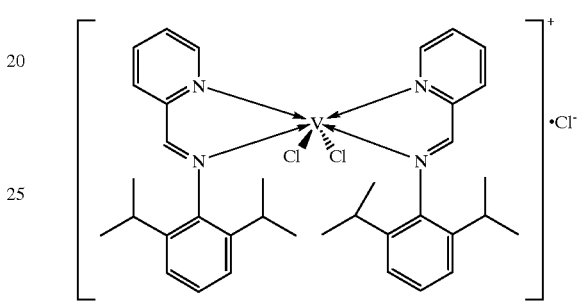

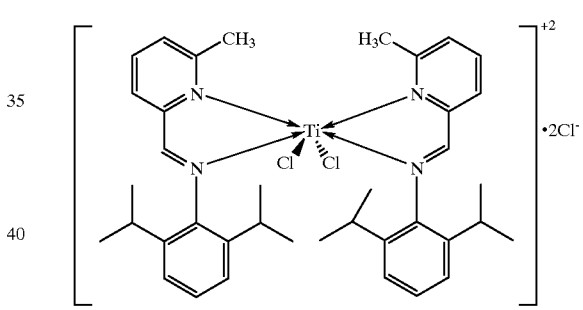

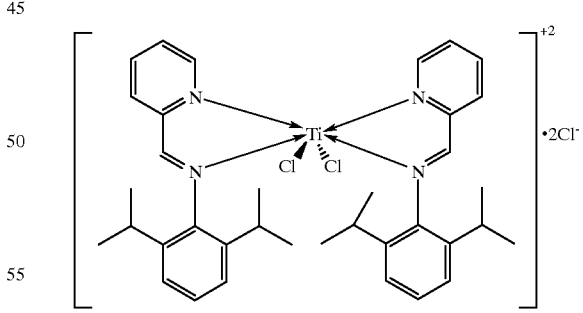

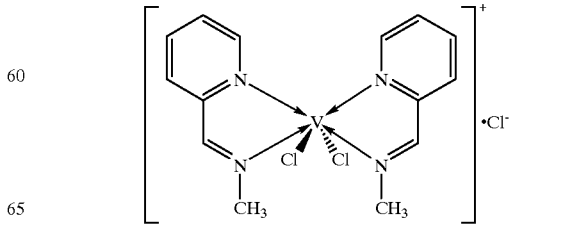

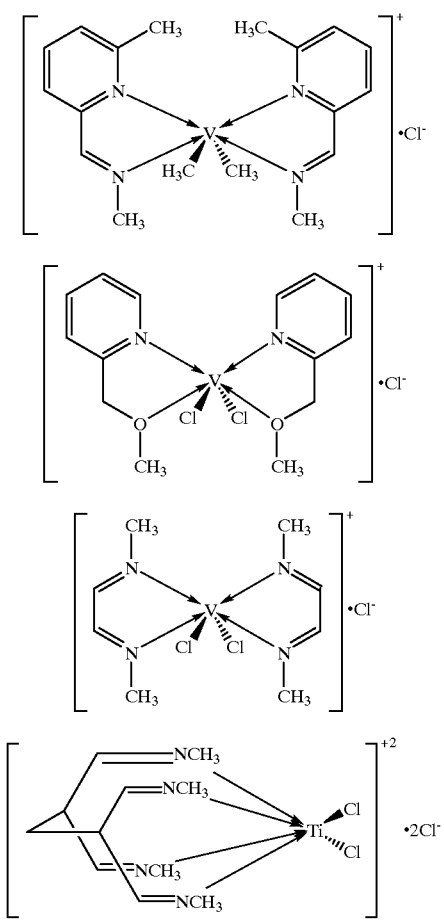

In a related embodiment, novel compounds are provided having the structure of formula (III)

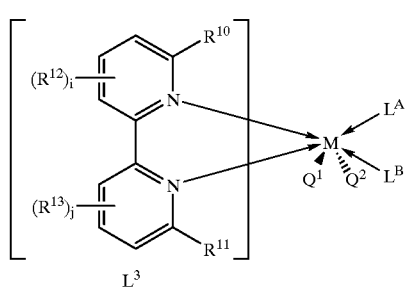

wherein i and j are independently zero, 1, 2 or 3, $R^{10}$, $R^{11}$, $R^{12}$ and $R^{13}$ are independently hydrocarbyl or substituted hydrocarbyl, and M, $Q^1$, $Q^2$, $L^A$ and $L^B$ are as defined previously, or $L^A$ and $L^B$ together represent an additional $L^3$ moiety.

Other complexes suitable as catalysts herein have the structure of formula (IV)

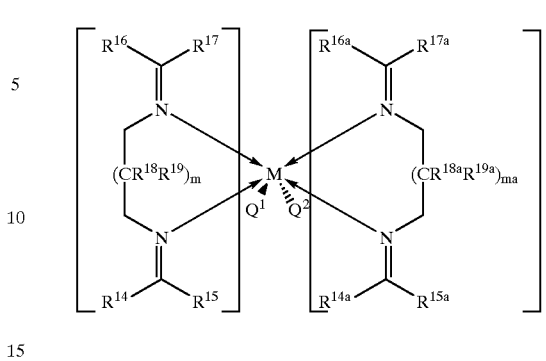

wherein:

M is a mid-transition metal, and $Q^1$ and $Q^2$ are as defined above for structural formula $R^{14}$ is hydrocarbyl or substituted hydrocarbyl, and $R^{15}$ is hydrido, hydrocarbyl or substituted hydrocarbyl, or $R^{14}$ and $R^{15}$ taken together form a ring;

$R^{14a}$ is hydrocarbyl or substituted hydrocarbyl, and $R^{15a}$ is hydrido, hydrocarbyl or substituted hydrocarbyl, or $R^{14a}$ and $R^{15a}$ taken together form a ring;

$R^{16}$ is hydrocarbyl or substituted hydrocarbyl, and $R^{17}$ is hydrido, hydrocarbyl or substituted hydrocarbyl, or $R^{16}$ and $R^{17}$ taken together form a ring;

$R^{16a}$ is hydrocarbyl or substituted hydrocarbyl, and $R^{17a}$ is hydrido, hydrocarbyl or substituted hydrocarbyl, or $R^{16a}$ and $R^{17a}$ taken together form a ring;

$R^{18}$, $R^{18a}$, $R^{19}$ and $R^{19a}$ are independently selected from the group consisting of hydrido to and hydrocarbyl, or one of $R^{18}$ and $R^{18a}$ may be bound to one of $R^{19}$ and $R^{19a}$ through a lower alkylene linkage; and m and ma are independently zero or 1.

Synthesis

The complexes of the invention are synthesized using any one of several techniques. In general, the complexes may be prepared using relatively simple and straightforward synthetic processes known to those skilled in the art and/or described in the pertinent texts and literature. In general, the novel complexes are prepared by first providing an unsaturated nitrogenous compound such as an imine-containing ligand to serve as "$L^1$," which can be obtained commercially or readily synthesized using techniques known to those skilled in the art of synthetic chemistry and/or are described in the pertinent literature. See, e.g., PCT Publication Nos. WO 98/27124, WO 98/30612 and WO 98/49208, and U.S. Pat. No. 5,866,663, all cited earlier herein. For example, a diimine ligand having the structural formula

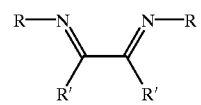

wherein R and R' are defined as any of $R^1$, $R^2$, $R^5$ and $R^6$, defined earlier herein with respect to compounds of formula (I), may be synthesized by addition of the primary amine R—$NH_2$ to the diketone

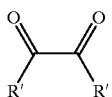

in a simple, straightforward, one-step reaction.

Other ligands containing one or more C=N groups may be synthesized in a similar manner, by reaction of a suitable primary amine with a selected aldehyde or a ketone. For example, the asymmetric ligand

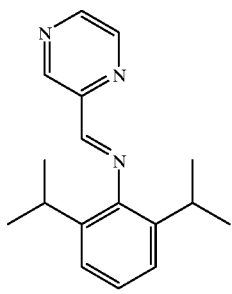

may be readily synthesized from 2,6-diisopropylaniline and 2-pyrazinecarboxaldehyde, as described, for example, in Weidenbruch et al. (1993) *Organometallic Chemistry* 454:3 5. Reference may also be had to Patai, *The Chemistry of the Carbon-Nitrogen Double Bond* (1970), which provides information on various synthetic methods that can be used in the preparation of imines.

The metal complexes are then synthesized using a metallation reaction in which at least one equivalent of the selected ligand or ligands are caused to react with a metal compound $MQ^1Q^2Y_2$ wherein M is a mid-transition metal, i.e., a Group VA, Group VIA or Group VIIA metal, $Q^1$ and $Q^2$ are as defined earlier herein, and the Y substituents are "leaving groups" that are generally selected from the group consisting of halide, pseudohalide (e.g., lower alkoxy such as methoxy), flurohydrocarbylborates, etc. During the metallation reaction, then, the Y groups are eliminated. Alternative metallation techniques are also possible, as will be appreciated by those skilled in the art. A suitable metallation reaction is described in Example 1, part (b). Other suitable metallation reactions for preparing the present compounds will be known to those skilled in the art and/or described in or readily derived from the pertinent texts and literature.

Preparation of the Catalyst System

The novel compounds of the invention, when used as polymerization catalysts, are used in conjunction with a conventional catalyst activator as will be appreciated by those skilled in the art. Thus, prior to use, the compounds of the invention are incorporated into a catalyst system which includes such an activator. Suitable catalyst activators include metal alkyls, hydrides, alkylhydrides, and alkylhalides, such as alkyllithium compounds, dialkylzinc compounds, trialkyl boron compounds, trialkylaluminum compounds, alkylaluminum halides and hydrides, and tetraalkylgermanium compounds. Specific examples of useful activators include n-butyllithium, diethylzinc, di-n-propylzinc, triethylboron, triethylaluminum, triisobutylaluminum, tri-n-hexylaluminum, ethylaluminum dichloride, dibromide and dihydride, isobutyl aluminum dichloride, dibromide and dihydride, di-n-propylaluminum chloride, bromide and hydride, diisobutyl-aluminum chloride, bromide and hydride, ethylaluminum sesquichloride, methyl aluminoxane ("MAO"), hexaisobutyl aluminoxane, tetraisobutyl aluminoxane, polymethyl aluminoxane, tri-n-octylaluminum, tetramethyl germanium, and the like. Other activators which are typically referred to as ionic cocatalysts may also be used; such compounds include, for example, $(C_6H_6)_3{}^+$, $C_6H_5-NH_2CH_3{}^+$, and fluorohydrocarbylboron compounds such as tetra(pentafluorophenyl)borate, sodium tetrakis[(bis-3,5-trifluoromethyl)phenyl]borate, $H+(OCH_2CH_3)_2[(bis-3,5-trifluoromethyl)phenyl]borate$, trityltetra(pentafluorophenyl)borate and tris(pentafluorophenyl) boron. Mixtures of activators may, if desired, be used. Generally, the catalyst activator is such that upon combination with a compound of the invention, a catalytically active ionic species results, i.e., the catalyst activator Z ionically associates with the catalyst $L^1[MQ^1Q^2]L^2$ to produce the catalytically active ionic species $(L^1[M^+Q^1Q^2]L^2)Z^-$.

For liquid phase or slurry polymerization, the catalyst and activator are generally mixed in the presence of inert diluents such as, for example, aliphatic or aromatic hydrocarbons, e.g., liquified ethane, propane, butane, isobutane, n-butane, n-hexane, isooctane, cyclohexane, methylcyclohexane, cyclopentane, methylcyclopentane, cycloheptane, methylcycloheptane, benzene, ethylbenzene, toluene, xylene, kerosene, Isopar® M, Isopar® E, and mixtures thereof. Liquid olefins or the like which serve as the monomers or comonomers in the polymerization process may also serve as the diluent; such olefins include, for example, ethylene, propylene, butene, 1-hexene and the like. The amount of catalyst in the diluent will generally be in the range of about 0.01 to 1.0 mmoles/liter, with activator added such that the ratio of catalyst to activator is in the range of from about 10:1 to 1:2000, preferably in the range of from about 1:1 to about 1:200, on a molar basis.

Preparation of the catalyst/activator/diluent mixture is normally carried out under anhydrous conditions in the absence of oxygen, at temperatures in the range of from about −90° C. to about 300° C., preferably in the range of from about −10° C. to about 200° C.

The catalyst, activator and diluent are added to a suitable reaction vessel, in any order, although, as noted above, the catalyst and activator are usually mixed in the diluent and the mixture thus prepared then added to the reactor.

Use in Polymerization

The novel catalysts are used to prepare polymeric compositions using conventional polymerization techniques known to those skilled in the art and/or described in the pertinent literature. The monomer(s), catalyst and catalyst activator are contacted at a suitable temperature at reduced, elevated or atmospheric pressure, under an inert atmosphere, for a time effective to produce the desired polymer composition. The catalyst may be used as is or supported on a suitable support. In one embodiment, the novel catalysts are used as homogeneous catalysts, i.e., as unsupported catalysts, in a gas phase or liquid phase polymerization process. A solvent may, if desired, be employed. The reaction may be conducted under solution or slurry conditions, in a suspension using a perfluorinated hydrocarbon or similar liquid, in the gas phase, or in a solid phase powder polymerization.

Liquid phase polymerization generally involves contacting the monomer or monomers with the catalyst/activator mixture in the polymerization diluent, and allowing reaction to occur under polymerization conditions, i.e., for a time and at a temperature sufficient to produce the desired polymer product. Polymerization may be conducted under an inert atmosphere such as nitrogen, argon, or the like, or may be conducted under vacuum. Preferably, polymerization is conducted in an atmosphere wherein the partial pressure of reacting monomer is maximized. Liquid phase polymerization may be carried out at reduced, elevated or atmospheric pressures. In the absence of added solvent, i.e., when the olefinic monomer serves as the diluent, elevated pressures are preferred. Typically, high pressure polymerization in the absence of solvent is carried out at temperatures in the range of about 180° C. to about 300° C., preferably in the range of about 250° C. to about 270° C., and at pressures on the order of 200 to 20,000 atm, typically in the range of about 1000 to 3000 atm. When solvent is added, polymerization is generally conducted at temperatures in the range of about 150° C. to about 300° C., preferably in the range of about 220° C. to about 250° C., and at pressures on the order of 10 to 2000 atm.

Polymerization may also take place in the gas phase, e.g., in a fluidized or stirred bed reactor, using temperatures in the range of approximately 60° C. to 120° C. and pressures in the range of approximately 10 to 1000 atm.

The monomer or comonomers used are addition polymerizable monomers containing one or more degrees of unsaturation. Olefinic or vinyl monomers are preferred, and particularly preferred monomers are α-olefins having from about 2 to about 20 carbon atoms, such as, for example, linear or branched olefins including ethylene, propylene, 1-butene, 3-methyl-1-butene, 1,3-butadiene, 1-pentene, 4-methyl-1-pentene, 1-hexene, 4-methyl-1-hexene, 1,4-hexadiene, 1,5-hexadiene, 1-octene, 1,6-octadiene, 1-nonene, 1-decene, 1,4-dodecadiene, 1-hexadecene, 1-octadecene, and mixtures thereof. Cyclic olefins and diolefins may also be used; such compounds include, for example, cyclopentene, 3-vinylcyclohexene, norbornene, 5-vinyl-2-norbornene, 5-ethylidene-2-norbornene, dicyclopentadiene, 4-vinylbenzocyclobutane, tetracyclododecene, dimethano-octahydronaphthalene, and 7-octenyl-9-borabicyclo-(3,3,1)nonane. Aromatic monomers which may be polymerized using the novel metallocenes include styrene, o-methylstyrene, m-methylstyrene, p-methylstyrene, p-tert-butylstyrene, m-chlorostyrene, p-chlorostyrene, p-fluorostyrene, indene, 4-vinylbiphenyl, acenaphthalene, vinylfluorene, vinylanthracene, vinylphenanthrene, vinylpyrene and vinylchrisene. Other monomers which may be polymerized using the present catalysts include methylmethacrylate, ethylacrylate, vinyl silane, phenyl silane, trimethylallyl silane, acrylonitrile, maleimide, vinyl chloride, vinylidene chloride, tetrafluoroethylene, isobutylene, carbon monoxide, acrylic acid, 2-ethylhexylacrylate, methacrylonitrile and methacrylic acid.

In gas and slurry phase polymerizations, the catalyst is used in a heterogeneous process, i.e., supported on an inert inorganic substrate. Conventional materials can be used for the support, and are typically particulate, porous materials; examples include oxides of silicon and aluminum, or halides of magnesium and aluminum. Particularly preferred supports from a commercial standpoint are silicon dioxide and magnesium dichloride.

The polymeric product resulting from the aforementioned reaction may be recovered by filtration or other suitable techniques. If desired, additives and adjuvants may be incorporated into the polymer composition prior to, during, or following polymerization; such compounds include, for example, pigments, antioxidants, lubricants and plasticizers.

The compounds of the invention are also useful in catalyzing other types of reactions, i.e., reactions other than polymerizations. Such reactions include, but are not limited to, hydrogenation, dehydrocoupling, cyclization, substitution, carbomagnesation and hydrosilylation. Methods for using the metal complexes of the invention to catalyze the aforementioned reactions and others will be known to those skilled in the art and/or described in the pertinent texts and literature.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

Experimental

The following examples are put forth so as to provide those of ordinary skill in the art with a complete disclosure and description of how to prepare and use the catalysts of the invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

All patents, patent applications, journal articles and other references mentioned herein are incorporated by reference in their entireties.

Examples 1 through 4 describe methods for synthesizing various complexes of the invention; Example 5 describes a procedure for preparing a catalyst system using the compounds of the invention, that is then used in the preparation of polyethylene; Example 6 describes preparation of LLDPE using a catalyst of the invention; and Example 7 describes preparation of isotactic polypropylene using a catalyst of the invention.

EXAMPLE 1

This example describes synthesis of a mid-transition metal complex of the invention, with ligand synthesis described in part (a) and metallation described in part (b).

(a) The imine-containing ligand 1 may be synthesized by reaction of phenyl 2-pyridine ketone with 2,6-diisopropylaniline as illustrated in Scheme 1 (in the scheme, "Ph" represents phenyl):

SCHEME 1

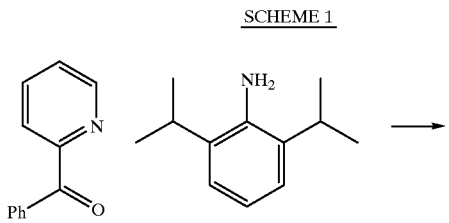

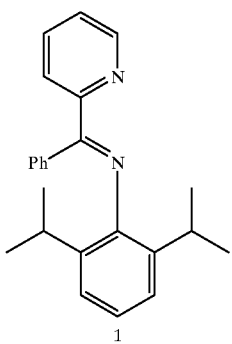

1

A 250-mL flask was charged with 2-benzoyl pyridine and methanol. A slight excess of 2,6-diisopropylaniline (1.1 eq) was added by pipet. The yellow mixture was stirred at room temperature in methanol for 1 d. The solvent and unreacted aniline was removed in vacuo to give the desired product as a yellow oil. $^1$H NMR (300 MHz, 296 K, CDCl$_3$): δ8.74(d, 1H), 8.06(m, 3H), 7.91(t, 1H), 7.60(d, 1H), 7.50(m, 3H), 7.05(d, 2H), 6.81(t, 1H), 2.93(sept, 2H), 1.28(d, 12H).

(b) The ligand synthesized in part (a) was then metallated with chromium trichloride as illustrated in Scheme 2, to yield metal complex 2:

SCHEME 2

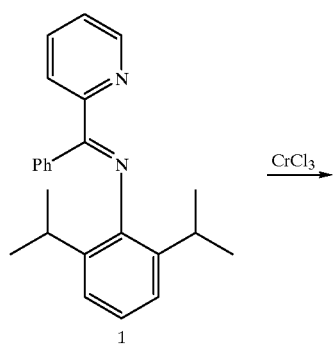

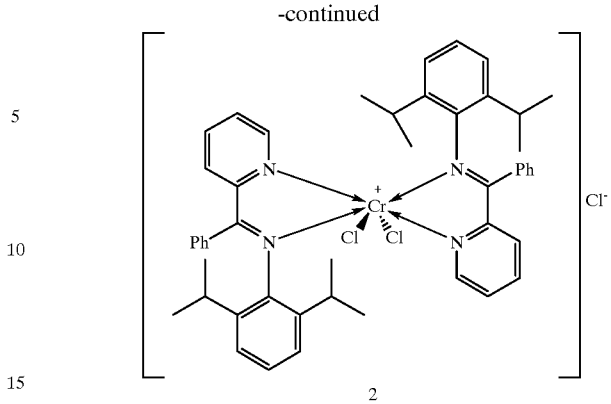

2

A 2:5 molar ratio of CrCl$_3$ to ligand 1 was dissolved in a methanol/1-propanol solution. A small amount of Zn dust was added, and the solution was heated to 100° C. and allowed to reflux for 4 hours. The solution was then slowly cooled to room temperature and stored, uncovered, for 30 hours. The solution was then heated at 105° C. for 3 hours, cooled to room temperature and then stored at −10° C. for 12 hours. Excess solvent was evaporated off and the remaining material dissolved in CH$_2$Cl$_2$. The complex 2 was precipitated out by the addition of ether to the CH$_2$Cl$_2$ solution. The complex was isolated as a purple microcrystalline powder. The yield was 32%.

EXAMPLE 2

This example describes synthesis of another mid-transition metal complex of the invention, with ligand synthesis as illustrated in Scheme 3 and described in part (a), and metallation as illustrated in Scheme 4 and described in part (b).

(a) The imine-containing ligand 3 may be synthesized by reaction of 2,6-pyrazine carboxaldehyde with 2,6-diisopropylaniline as illustrated in Scheme 3:

SCHEME 3

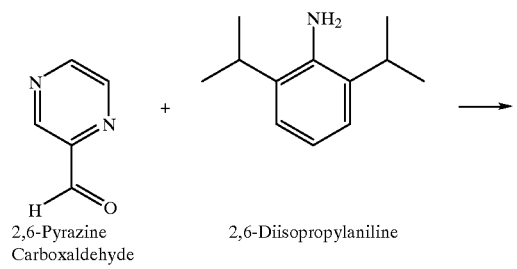

2,6-Pyrazine Carboxaldehyde     2,6-Diisopropylaniline

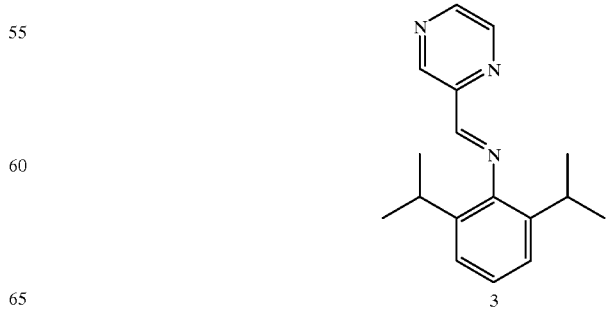

3

A 250-mL flask is charged with 2,6-pyrazine carboxaldehyde and methanol. A slight excess of 2,6-diisopropylaniline (1.1 eq) is added by pipet. The mixture is stirred at room temperature in methanol for 1 d. The solvent and unreacted aniline are removed in vacuo to give the desired product.

(b) Metallation: The ligand synthesized in part (a), 3, is then metallated with titanium tetrachloride as illustrated in Scheme 4, to yield metal complex 4:

SCHEME 4

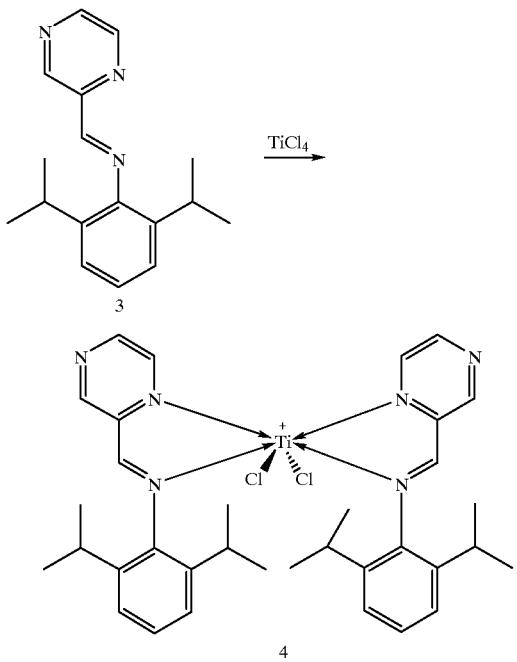

4

A 2:5 molar ratio of TiCl$_4$ to ligand 3 is dissolved in a methanol/1-propanol solution. Then, the reagents and procedures in Example 1, part (b) are then used to yield the desired metal complex 4.

EXAMPLE 3

This example describes synthesis of an additional mid-transition metal complex 5 of the invention as illustrated in Scheme 5.

SCHEME 5

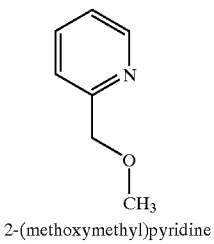

2-(methoxymethyl)pyridine

-continued

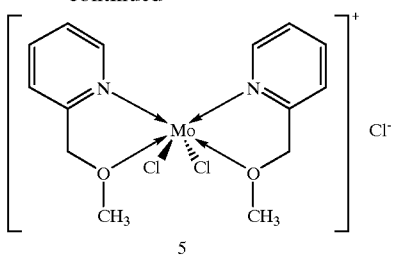

5

A 2:5 molar ratio of MoCl$_3$ to 2-(methoxymethyl)-pyridine is dissolved in a methanol/1-propanol solution. A dash of Zn dust is added and the solution heated to 100° C. and allowed to reflux for 4 hours. The reagents and procedures of Example 1, part (b), are then used to yield the desired metal complex 5.

EXAMPLE 4

This example describes synthesis of another mid-transition metal complex of the invention, with synthesis of a first ligand described in part (a), and metallation described in part (b). The second ligand, bipyridine, may be obtained commercially.

(a) Synthesis of first ligand: The imine-containing ligand 6 may be synthesized by reaction of glyoxal with 2,6-diisopropylaniline as illustrated in Scheme 6.

SCHEME 6

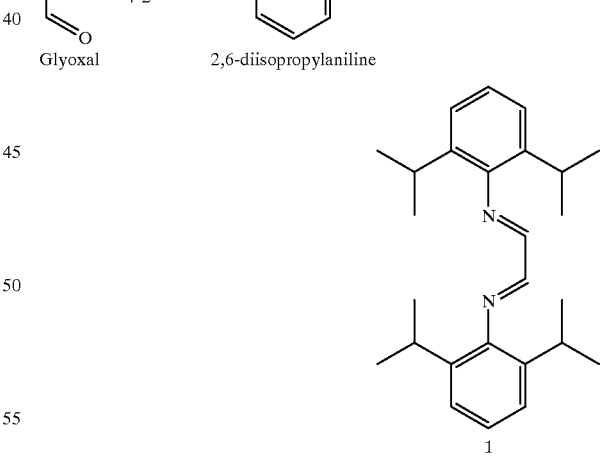

An approximately 2:1 molar ratio mixture of aniline to glyoxal is heated to about 100° C. and stirred at this temperature for 15 minutes. Crystallization of the crude reaction mixture from cold pentane yields the desired ligand 6.

(b) Metallation: The ligand synthesized in part (a) and a second ligand, bipyridine, are then metallated with MoCl$_3$ as illustrated in Scheme 7, to yield metal complex 7:

SCHEME 7

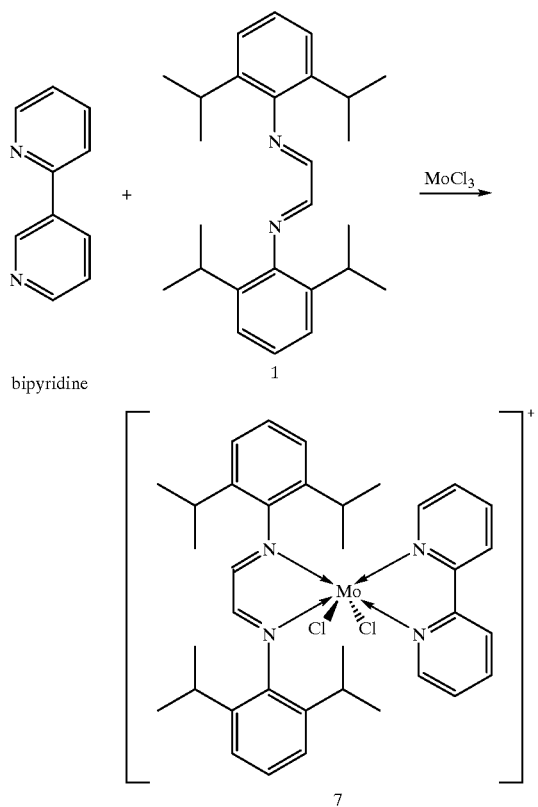

A equimolar ratio of MoCl$_3$, ligand 6 and bipyridine is dissolved in a methanol/1-propanol solution. A dash of Zn dust is added and the solution heated to 100° C. and allowed to reflux for 4 hours. The reagents and procedures of Example 1, part (b), are then used to prepare the desired metal complex 7.

EXAMPLE 5

Preparation of a Catalyst System and Use in the Polymerization of Ethylene

The metal complex prepared in Example 1 was used as the polymerization catalyst in the preparation of polyethylene ("PE"), as follows:

A 300-mL autoclave was charged with toluene (100 mL), ethylene (100 psig), and the catalyst prepared in example 1 (10 mg, 0.012 mmol) at 25 ° C. A solution of methyl aluminoxane (MAO) (4.0 g, 10% in toluene, [Al]/[Cr]=583) was injected to initiate the polymerization. After 1 h, the reaction was quenched by venting the ethylene. The polymer was collected, washed with methanol, and dried in a vacuum oven overnight. Yield =11.43 g.

EXAMPLE 6

Preparation of Linear Low Density Polyethylene

The metal complexes prepared in any one of Examples 1–4 are used as polymerization catalysts in the preparation of linear low density polyethylene ("LLDPE"). Standard ethylene polymerization conditions are used, as follows:

Polymerizations are conducted in a 300 mL autoclave reactor. Methyl aluminoxane (MAO) is used as co-catalyst with total Al/Metal ratio equal to 1000. Prior to initiation of polymerization, the reactors are loaded with 160 mL of toluene and the MAO. The reactors are heated to 50° C. and pressurized with a mixture of ethylene and 1-butene to 40 psig. The 1-butene represents approximately 5 to 15 mole % of the monomer mixture and, as will be appreciated by those skilled in the are, can be substituted with an alternative olefinic monomer such as 1-hexene, 1-octene or 4-methyl-1-pentene. The reactors are configured to maintain the set pressure and temperature during the polymerization reaction. The reaction is initiated by injection of the catalyst. The reactions are run for 30 minutes and terminated by injection of acidified methanol (2% HCl). The polymer is removed from the reactor, precipitated out with acidified methanol, collected on a fritted glass filter and dried in a vacuum oven overnight.

EXAMPLE 7

Preparation of Isotactic Polypropylene

The complex prepared in Example 1 is used as a polymerization catalyst in the preparation of isotactic polypropylene. Standard propylene polymerization conditions are used, as follows:

Polymerizations are conducted in a 300 mL autoclave reactor. Methyl aluminoxane (MAO) is used as co-catalyst with total Al/Metal ratio equal to 1000. Prior to initiation of polymerization, the reactors are loaded with 160 mL of toluene and the MAO. The reactors are heated to 50° C. and pressurized with propylene to 40 psig. The reactors are configured to maintain the set pressure and temperature during the polymerization reaction. The reaction is initiated by injection of the catalyst. The reactions are run for 30 minutes and terminated by injection of acidified methanol (2% HCl). The isotactic polymer is removed from the reactor, precipitated out with acidified methanol, collected on a fritted glass filter and dried in a vacuum oven overnight.

EXAMPLE 8

Preparation of Syndiotactic Polypropylene

The complex prepared in Example 4 is used as a polymerization catalyst in the preparation of syndiotactic polypropylene. Standard propylene polymerization conditions are used, as follows:

Polymerizations are conducted in a 300 mL autoclave reactor. Methyl aluminoxane (MAO) is used as co-catalyst with total Al/Metal ratio equal to 1000. Prior to initiation of polymerization, the reactors are loaded with 160 mL of toluene and the MAO. The reactors are heated to 50° C. and pressurized with propylene to 40 psig. The reactors are configured to maintain the set pressure and temperature during the polymerization reaction. The reaction is initiated by injection of the catalyst. The reactions are run for 30 minutes and terminated by injection of acidified methanol (2% HCl). The syndiotactic polymer is removed from the reactor, precipitated out with acidified methanol, collected on a fritted glass filter and dried in a vacuum oven overnight.

What is claimed is:

1. A method for preparing a polymer composition, comprising:
    contacting, under polymerization conditions, an addition polymerizable monomer having at least one degree of unsaturation with a catalyst system comprised of:
    (a) a catalyst having the structural formula L$^1$[MQ$^1$Q$^2$] L$^2$ in which M is a mid-transition metal selected from the group consisting of Nb, Ta, Mo, W, Mn and Re, $Q^1$ and $Q^2$ are each a univalent radical, and $L^1$ and $L^2$ are ligands coordinated to M, wherein each of $L^1$ and $L^2$ contains a first coordinating atom that is a nitrogen atom contained within a C=N group, and a second coordinating atom that is either a second nitrogen atom, optionally present in a second C=N group, or an oxygen, sulfur or phosphorus atom; and (b) a catalyst activator effective to produce a catalytically active ionic species when combined with said catalyst.

2. The method of claim 1, wherein the addition polymerizable monomer is an olefinic or vinyl monomer.

3. The method of claim 2, wherein the addition polymerizable monomer is ethylene.

4. The method of claim 2, wherein the addition polymerizable monomer is propylene.

5. A method for synthesizing an isotactic polyolefin, comprising:

providing an isospecific catalyst having the structural formula $L^1[MQ^1Q^2]L^2$ in which M is a mid-transition metal selected from the group consisting of Nb, Ta, Mo, W, Mn and Re, $Q^1$ and $Q^2$ are each a univalent radical, and $L^1$ and $L^2$ are identical ligands coordinated to M, each containing a first coordinating nitrogen atom contained within a first C=N group and bound to a first substituent $R_S$ and a second coordinating nitrogen atom contained within a second C=N group and bound to a second substituent $R_L$, wherein the difference in steric bulk between $R_S$ and $R_L$ is effective to provide an isotactic polymerization product;

admixing the catalyst with a catalyst activator, to produce a catalyst system; and contacting, under polymerization conditions, an olefinic monomer $CH_2$=$CH_2(R)$ wherein R is other than hydrogen, with the catalyst system.

6. The method of claim 5, wherein R is methyl and the isotactic polyolefin is isotactic polypropylene.

7. A method for synthesizing a syndiotactic polyolefin, comprising:

providing a syndiospecific catalyst having the structural formula $L^1[MQ^1Q^2]L^2$ in which M is a mid-transition metal selected from the group consisting of Nb, Ta, Mo, W, Mn and Re, $Q^1$ and $Q^2$ are each a univalent radical, and $L^1$ and $L^2$ are different ligands coordinated to M, each containing a first coordinating nitrogen atom contained within a first C=N group and a second coordinating nitrogen atom contained within a second C=N group, wherein the first and second coordinating nitrogen atoms in the ligand $L^1$ are bound to a first substituent $R_S$, and the first and second coordinating nitrogen atoms in the ligand $L^2$ are bound to a second substituent $R_L$, and further wherein the difference in steric bulk between $R_S$ and $R_L$ is effective to provide a syndiotactic polymerization product;

admixing the catalyst with a catalyst activator, to produce a catalyst system; and contacting, under polymerization conditions, an olefinic monomer $CH_2$=$CH_2(R)$ wherein R is other than hydrogen, with the catalyst system.

8. The method of claim 7, wherein R is methyl and the syndiotactic polyolefin is syndiotactic polypropylene.

9. A method for synthesizing linear low density polyethylene (LLDPE), comprising:

providing a catalyst having the structural formula $L^1[MQ^1Q^2]L^2$ in which M is a mid-transition metal selected from the group consisting of Nb, Ta, Mo, W, Mn and Re, $Q^1$ and $Q^2$ are each a univalent radical, and $L^1$ and $L^2$ are ligands coordinated to M, wherein each of $L^1$ and $L^2$ contains a first coordinating atom that is a nitrogen atom contained within a C=N group, and a second coordinating atom that is either a second nitrogen atom, optionally present in a second C=N group, or an oxygen, sulfur or phosphorus atom;

admixing the catalyst with a catalyst activator, to produce a catalyst system; and contacting, under polymerization conditions, a mixture of olefinic monomers with the catalyst system, wherein the mixture comprises ethylene and a second olefinic co-monomer $CH_2$=CHR, wherein R is a $C_4$–$C_8$ alkyl group.

10. The method of claim 9, wherein the second olefinic co-monomer represents approximately 5 mole % to 15 mole % of the mixture.

11. The method of claim 10, wherein the second olefinic co-monomer is selected from the group consisting of 1-butene, 1-hexene, 1-octene, 4-methyl-1-pentene, and mixtures thereof.

12. The method of claim 1, wherein, in each of $L^1$ and $L^2$, the second coordinating atom is a second nitrogen atom.

13. The method of claim 12, wherein, in each of $L^1$ and $L^2$, the second nitrogen atom is present in a second C=N group.

14. The method of claimed, wherein $L^1$ and $L^2$ are identical.

15. The method of claim 14, wherein the first nitrogen atom in each of $L^1$ and $L^2$ is bound to a first substituent $R_S$, and the second nitrogen atom in each of $L^1$ and $L^2$ is bound to a second substituent $R_L$, wherein the difference in steric bulk between $R_S$ and $R_L$ is sufficient to result in isospecificity when the compound is used as a polymerization catalyst.

16. The method of claim 13, wherein $L^1$ and $L^2$ are different.

17. The method of claim 16, wherein the first and second nitrogen atoms in the ligand $L^1$ are bound to a first substituent $R_S$, and the first and second nitrogen atoms in the ligand $L^2$ are bound to a second substituent $R_L$, wherein the difference in steric bulk between $R_S$ and $R_L$ is sufficient to result in syndiospecificity when the compound is used as a polymerization catalyst.

18. The method of claim 1, wherein the catalyst has the structure of formula (II)

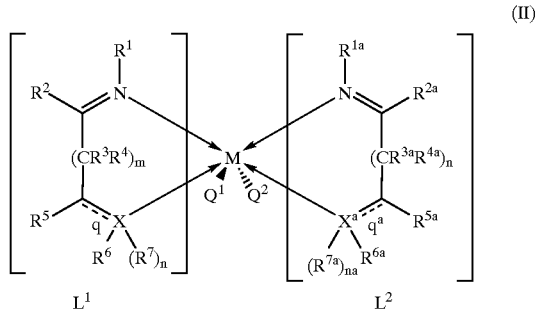

wherein:

wherein:

M is a mid-transition metal;

$Q^1$ and $Q^2$ are independently selected from the group consisting of hydrido, halide, alkoxy, amido, unsubstituted $C_1$–$C_{30}$ hydrocarbyl, $C_1$–$C_{30}$ hydrocarbyl substituted with one or more substituents such as electron-withdrawing groups, and $C_1$–$C_{30}$ hydrocarbyl-substituted Group IVB elements, or $Q^1$ and $Q^2$ may together form an alkylidene olefin, acetylene, or a five- or six-membered cyclic hydrocarbyl group;

m and n are independently zero or 1;

q is an optional double bond;

X is N, O, S or P, with the provisos that (a) when X is N or P, then either n is 1 or q is present as a double bond, but not both, and (b) when X is O or S, then n is zero and q is absent;

$R^1$, $R^6$, and $R^7$ are independently hydrido, hydrocarbyl or substituted hydrocarbyl, and $R^2$ and $R^5$ are independently hydrido, halo, hydrocarbyl or substituted hydrocarbyl, or $R^1$ and $R^2$ and/or $R^5$ and $R^6$ may be taken together to form a linkage —Q—, resulting in a five- or six-membered ring, wherein Q is —[$(CR)_a(Z)_b$]— in which a is 2, 3 or 4, Z is N, O or S, b is zero or 1, the sum of a and b is 3 or 4, and R is selected from the group consisting of hydrido, halo, hydrocarbyl, hydrocarbyloxy, trialkylsilyl, $NR^8{}_2$, $OR^9$, and $NO_2$, wherein $R^8$ and $R^9$ are each independently hydrocarbyl, or wherein R moieties on adjacent carbon atoms may be linked to form an additional five- or six-membered ring, or $R^2$ and $R^5$ may together form a linkage —Q— as just defined;

$R^3$ and $R^4$ are independently selected from the group consisting of hydrido and hydrocarbyl, or at least one of $R^3$ and $R^4$ may be bound through a lower alkylene linkage to an atom contained within $L^A$ or $L^B$;

$L^A$ and $L^B$ are ligands which may be the same or different and are independently selected from the group consisting of nitrogen-containing, sulfur-containing and oxygen-containing heterocycles, tertiary amines and phosphines, or $L^A$ and $L^B$ may together form a single bidentate ligand that may or may not be the same as $L^1$, with the proviso that when (i) $L^A$ and $L^B$ form a single bidentate ligand that is identical to $L^1$ and M is V or Cr, then either (ii) $R^1$ and $R^2$ or $R^5$ and $R^6$ are taken together to form a linkage —Q— as defined above, or (iii) X is other than N, or both (ii) and (iii); and further wherein $q^a$, ma, na, and $R^{1a}$ through $R^{7a}$ are defined as for q, m, n and $R^1$ through $R^7$, respectively.

19. The method of claim 18, wherein the catalyst has a positive charge +y and is associated with y/z anions each bearing a negative charge –z.

20. The method of claim 19, wherein y and z are independently integers in the range of 1 to 4 inclusive.

21. The method of claim 20, wherein y and z are independently 1 or 2.

22. The method of claim 18, wherein the anions are selected from the group consisting of halide and pseudohalide.

23. The method of claim 18, wherein the catalyst has the structure of formula (V)

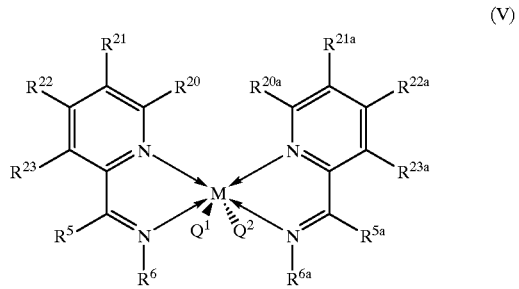

(V)

wherein:

$R^{20}$, $R^{20a}$, $R^{21}$, $R^{21a}$, $R^{22}$, $R^{22a}$, $R^{23}$ and $R^{23a}$ are hydrido or hydrocarbyl of 1 to 10 carbon atoms, or any two adjacent $R^{20}$, $R^{20a}$, $R^{21}$, $R^{21a}$, $R^{22}$, $R^{22a}$, $R^{23}$ and $R^{23a}$ groups may be linked to form a five- or six-membered aromatic ring.

24. The method of claim 23, wherein $R^{20}$, $R^{20a}$, $R^{21}$, $R^{21a}$, $R^{22}$, $R^{22a}$, $R^{23}$ and $R^{23a}$ hydrido.

25. The method of claim 23, wherein $R^{20}$ and $R^{20a}$ are methyl, and $R^{21}$, $R^{21a}$, $R^{22}$, $R^{22a}$, $R^{23}$ and $R^{23a}$ are hydrido.

26. The method of any one of claims 1, 5, 7 or 9, wherein the catalyst activator is aluminum-containing or boron-containing.

27. The method of claim 26, wherein the catalyst activator is aluminum-containing.

28. The method of claim 27, wherein the catalyst activator is an organoaluminum compound.

29. The method of claim 28, wherein the catalyst activator is an alkyl aluminoxane.

30. The method of claim 29, wherein the catalyst activator is methyl aluminoxane.

31. The method of claim 26, wherein the catalyst activator is boron-containing.

32. The method of claim 31, wherein the catalyst activator is a fluorohydrocarbylboron compound.

33. The method of claim 32, wherein the catalyst activator is a fluorinated phenylborate.

34. The method of any one of claims 1, 5, 7 or 9, wherein the catalyst system further includes an inert polymerization diluent.

35. The method of claim 34, wherein the diluent is a volatile hydrocarbon solvent.

* * * * *